(12) United States Patent
Murphy et al.

(10) Patent No.: US 9,528,968 B2
(45) Date of Patent: Dec. 27, 2016

(54) ENHANCED SENSITIVITY OF DETECTION IN ELECTROSPRAY IONIZATION MASS SPECTROMETRY USING A POST-COLUMN MODIFIER AND A MICROFLUIDIC DEVICE

(71) Applicant: Waters Technologies Corporation, Milford, MA (US)

(72) Inventors: James P. Murphy, Franklin, MA (US); Angela Doneanu, Franklin, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 0 days.

(21) Appl. No.: 14/881,395

(22) Filed: Oct. 13, 2015

(65) Prior Publication Data

US 2016/0131620 A1    May 12, 2016

Related U.S. Application Data

(60) Provisional application No. 62/063,627, filed on Oct. 14, 2014.

(51) Int. Cl.
| | |
|---|---|
| *H01J 49/10* | (2006.01) |
| *G01N 30/72* | (2006.01) |
| *G01N 30/32* | (2006.01) |
| *G01N 30/06* | (2006.01) |

(52) U.S. Cl.
CPC .......... *G01N 30/7266* (2013.01); *G01N 30/06* (2013.01); *G01N 30/32* (2013.01); *G01N 2030/326* (2013.01)

(58) Field of Classification Search
USPC ................................. 250/281, 282, 283, 288
See application file for complete search history.

(56) References Cited

U.S. PATENT DOCUMENTS

| | | | |
|---|---|---|---|
| 7,178,386 B1* | 2/2007 | Gamble | G01N 30/466 210/198.2 |
| 2012/0153143 A1* | 6/2012 | Kennedy | H01J 49/165 250/282 |
| 2013/0078624 A1* | 3/2013 | Holmes | C12Q 1/00 435/6.11 |

* cited by examiner

*Primary Examiner* — Nicole Ippolito
(74) *Attorney, Agent, or Firm* — McCarter & English, LLP; Deborah M. Vernon

(57) ABSTRACT

A microfluidic liquid chromatography-electrospray ionization (LC-ESI) device is provided for enhancing the sensitivity of mass spectrometric detection of an analyte in a sample. The device is designed to drive effective intermixing of an analytical flow stream exiting a chromatographic stationary phase and a post-column modifier reagent. The mixed flow stream thus obtained is used for generating an electrospray containing analyte ions. Also provided are methods for enhanced sensitivity of detection of an analyte in a sample.

21 Claims, 11 Drawing Sheets

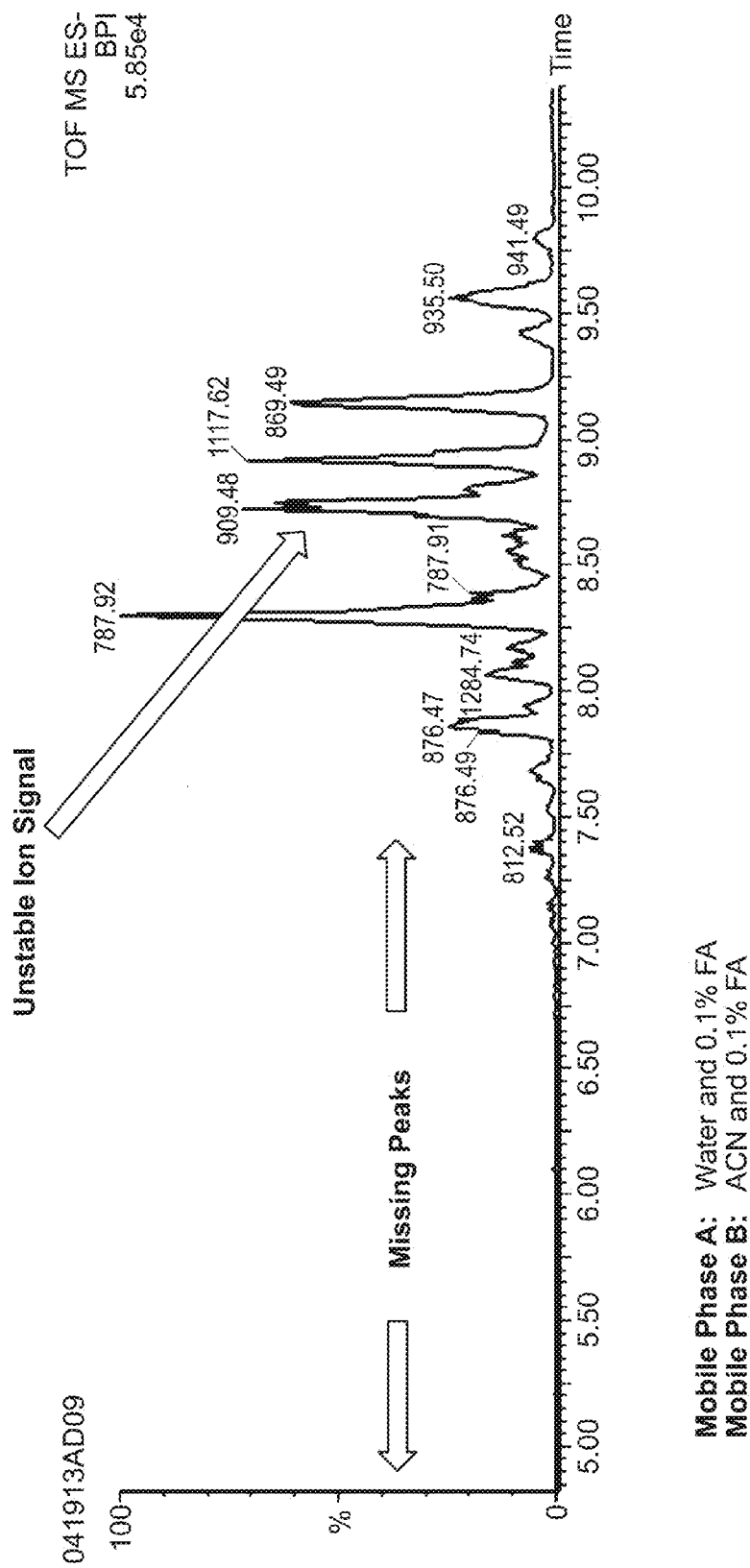

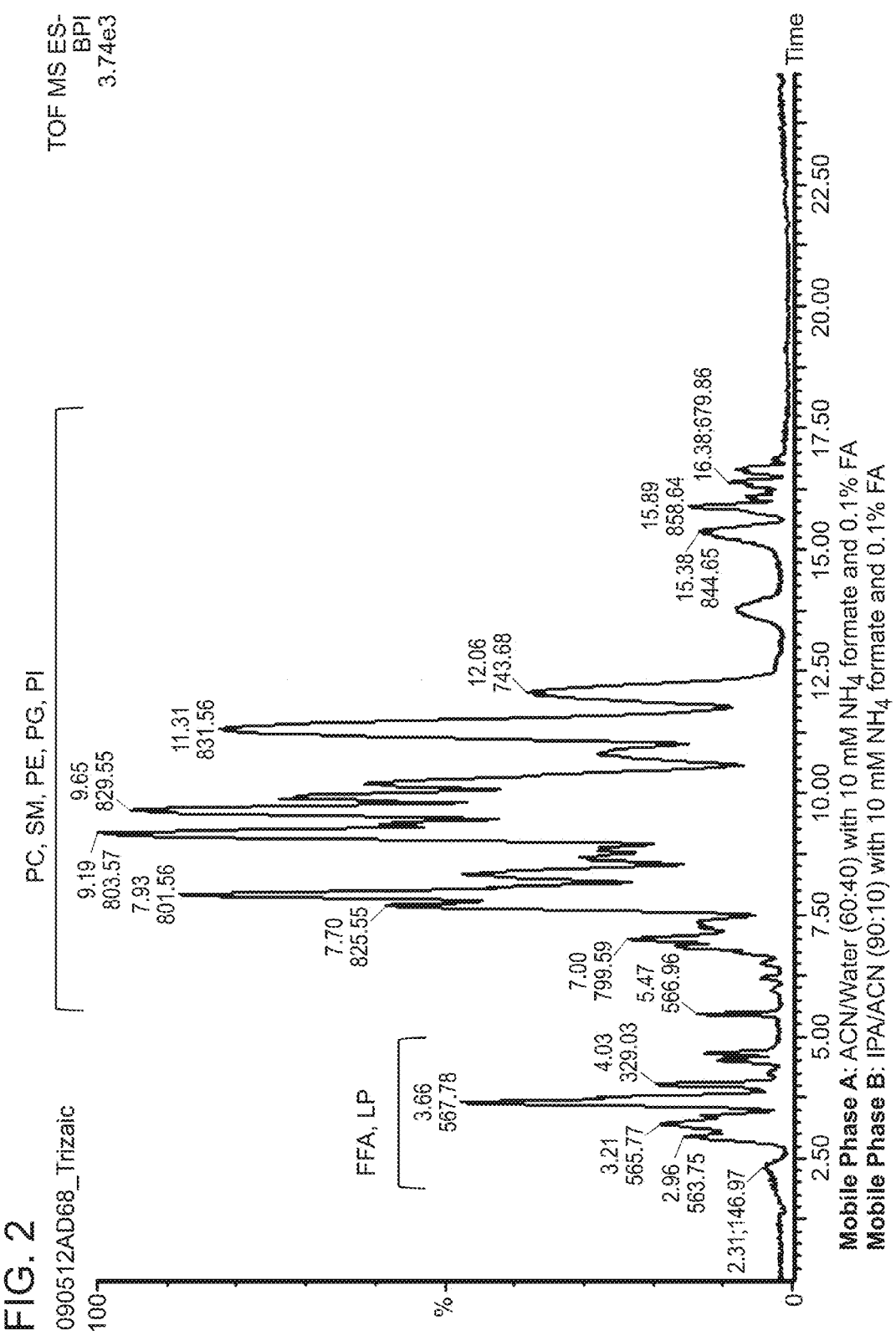

Method for enhanced detection of an analyte using a LC-ESI device, a gradient mobile phase, a post-column modifier reagent, and a mass spectrometer

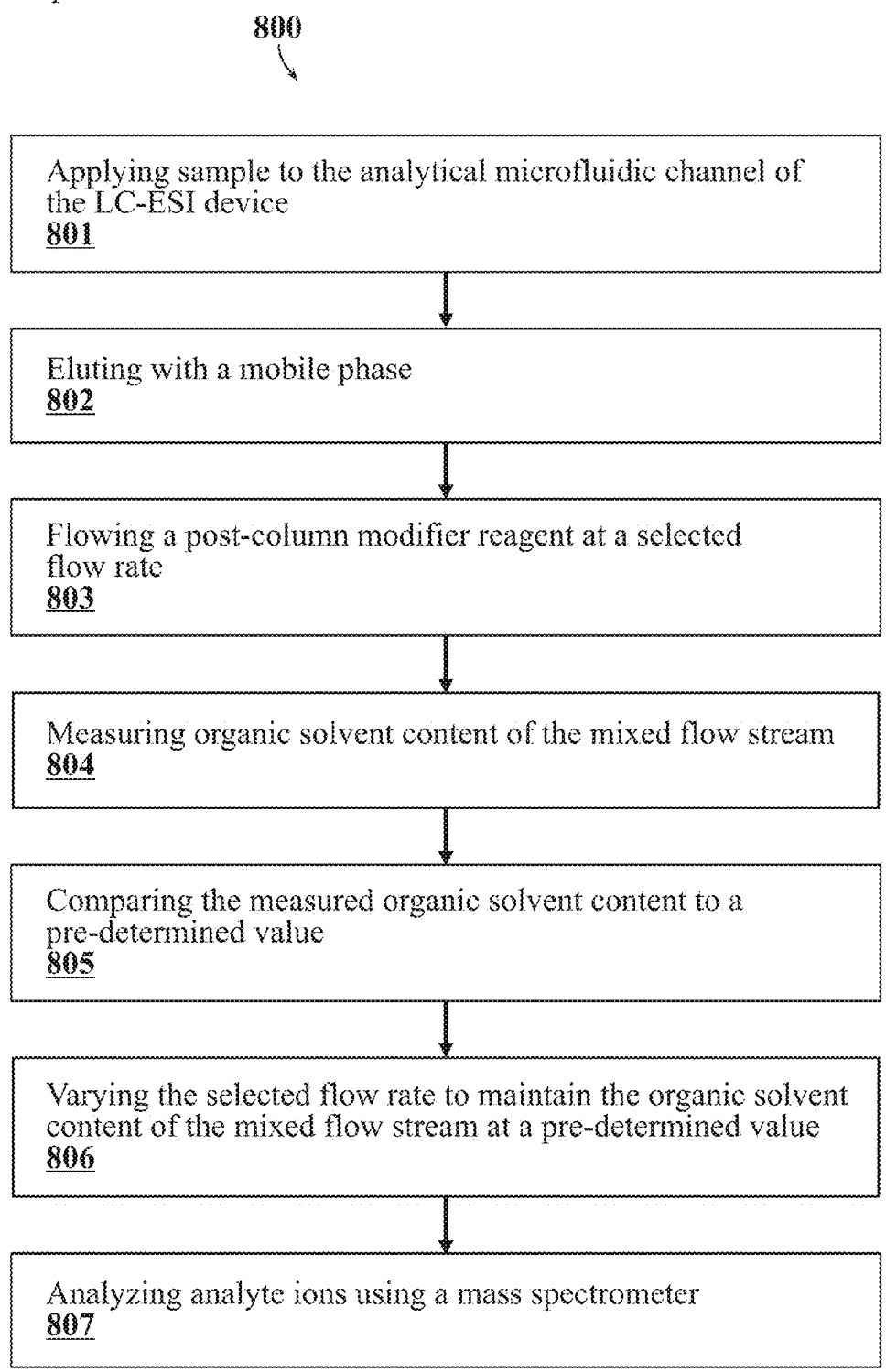

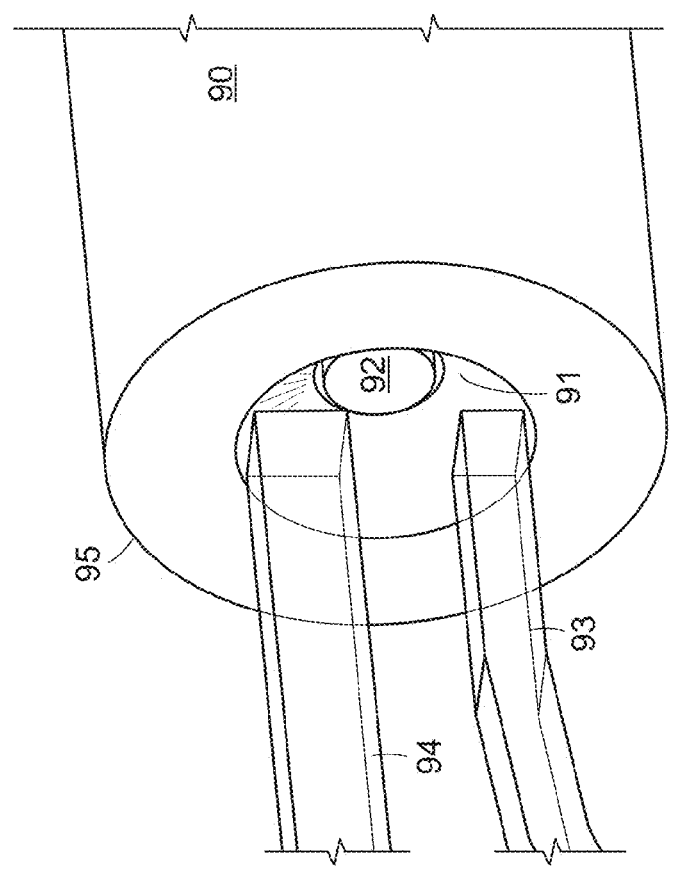
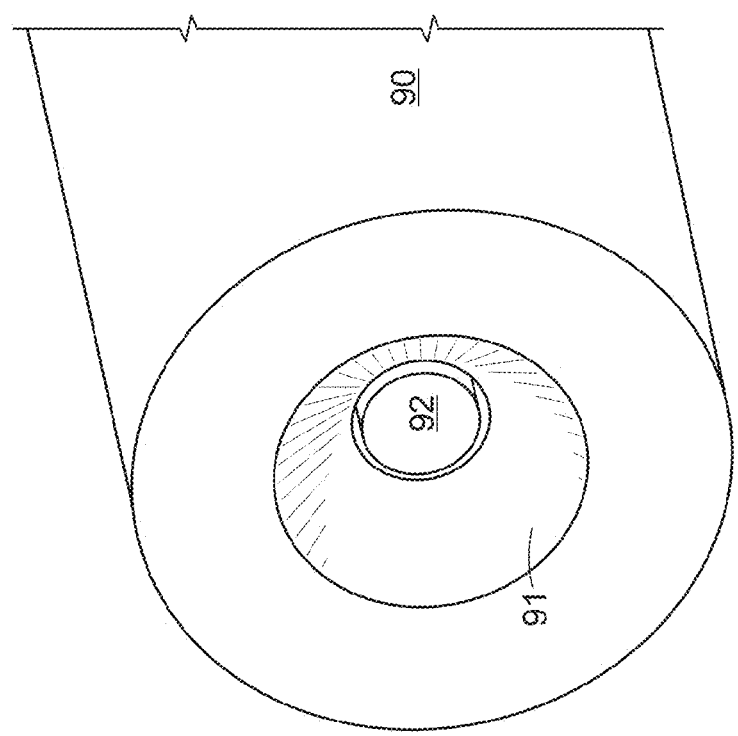
FIG. 9B
FIG. 9A

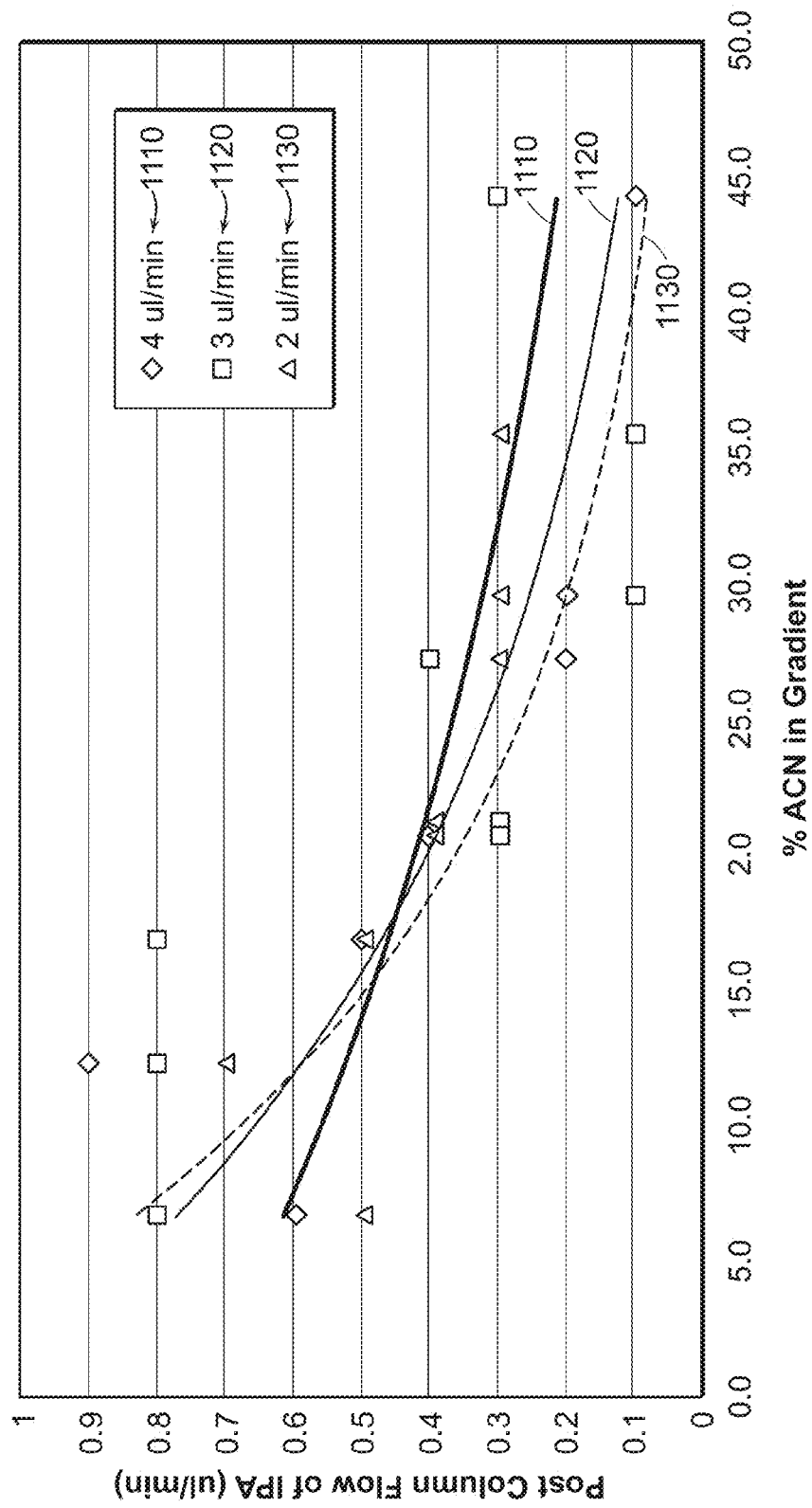

ENHANCED SENSITIVITY OF DETECTION IN ELECTROSPRAY IONIZATION MASS SPECTROMETRY USING A POST-COLUMN MODIFIER AND A MICROFLUIDIC DEVICE

RELATED APPLICATIONS

This application claims the benefit of and priority to U.S. provisional application No. 62/063,627, filed Oct. 14, 2014, the contents of which are hereby incorporated by reference in their entirety.

FIELD OF INVENTION

The present disclosure relates to methods and apparatus for increasing the sensitivity of detection of analytes in a liquid chromatography-electrospray ionization mass spectrometry.

BACKGROUND

Liquid chromatography electrospray ionization mass spectrometry (LC-ESI-MS) is a technique that combines the resolving power of high performance liquid chromatography (HPLC) separation with the high accuracy of a mass spectrometer (LC-MS) to achieve high sensitivity separation of analytes using an electrospray ionization (ESI) interface. Mass spectrometry typically involves ionization of chemical compounds to generate charged molecules or molecule fragments for determining the mass to charge ratios. Mass spectrometers remove target components as ions in a gas phase. Following removal, the ions migrate toward the detector of the mass spectrometer under high vacuum.

Liquid chromatography-Mass spectroscopy involves generation of gaseous ions from the liquid eluate exiting the chromatographic separation column. In this regard LC-MS is different from its precursor technology Gas chromatography-Mass Spectroscopy (GCMS) in which the target components, having already been gasified in the GC unit for separation, are introduced directly into the MS unit without further processing. However, if the LC unit were to be connected to the MS unit without an interface, the liquid mobile phase would vaporize and a large amount of gas would be introduced into the mass spectrometer decreasing the vacuum level and preventing the target ions from reaching the detector. Therefore, a major issue in LC-MS was the removal of the mobile phase, and an interface was needed that could convert the eluate of the LC into a reliable source of target ions.

The development of the atmospheric phase ionization (API) technique provided one such interface. Specifically, samples processed using the API technique, are ionized under atmospheric pressure and the solvent or the mobile phase removal takes place outside the vacuum of the spectrometer. Two main types of API interfaces based on different ionization principles are known. They are electrospray ionization (ESI), and atmospheric pressure chemical ionization (APCI). In general, ESI is best suited for ionic compounds with high polarity, and APCI is better suited for low or medium polarity compounds. The principles of ESI and representative ESIMS apparatus are described, for example, in US patents of Smith et al. (U.S. Pat. Nos. 4,842,701, 4,885,706), and Fenn (U.S. Pat. No. 6,297,499) among others, and in the review articles Fenn et al., Science 246, 64 (1989), and Smith et al., Analytical Chemistry 2, 882 (1990) among others.

Some features of the ESI technique are described below to highlight the ESI parameters that influence the sensitivity of detection by LC-ESI-MS. In general, a sample solution is drawn to the tip of a stainless steel capillary which is surrounded by a chamber, commonly referred to as the electrospray chamber. The walls of the electrospray chamber serve as electrodes subjecting the sample to a relatively high voltage of about 3 to 5 kV. The pressure in the chamber is typically maintained at one atmosphere. The capillary is also surrounded by a flow of a nebulizer gas to help generate a spray of the sample. The combination of the electric field and the nebulizer gas causes the liquid emerging from the capillary to be dispersed into a fine spray of charged droplets containing ions of the target. The charged solute molecules or the target ions of the droplets migrate to the surface due to repulsion. As the charged droplets move toward the mass spectrometer, the solvent evaporates causing the droplets to shrink. As a result, charge density in the droplets increase eventually reaching a limit known as the Rayleigh limit. The Rayleigh limit is a theoretical limit at which the applied electric field just counterbalances the surface tension of the droplets. See for example, (Wilm M. (2011) Principles of Electrospray Ionization; Mol. Cell. Proteomics. 10(7): M111.009407. As this limit is crossed, the electrostatic repulsion exceeds the surface tension of the solvent and the droplet explodes into smaller droplets. The solvent continues to evaporate and the sequence of evaporation and explosion continues until the droplet becomes so small that even at a charge density below the Raleigh limit, target ions begin to desorb (Ion Desorption Model). According to another proposed mechanism, eventually the droplets become so small that they contain only one target ion which is released when the solvent evaporates (Charge Residue Mechanism).

Electrospray ionization may be carried out in either positive or negative mode. In positive ion mode, the analyte is sprayed at low pH to encourage positive ion formation. In negative ion mode, the analysis is normally carried out well above a molecules isoelectric point to deprotonate the molecule.

For an electrospray ionization interface to function as a reliable source of target ions it is essential that the interface produce a stable spray. Stability is dependent upon a balance between flow rate and applied field. This balance is strongly influenced by solvent properties, particularly the electrical conductivity and surface tension of the solvent. In general, higher conductivity and surface tension require the flow rate to be reduced. And as a result, desirable flow rates for electrospray ionization are found to be in the μL/min range. As a solvent, water is a poor choice for conventional electrospray ionization relative to many common organic solvents (e.g. acetonitrile) because it has both high conductivity and high surface tension. The higher the surface tension the larger the voltage needed for ionization. Therefore, in an LC-ESI-MS analysis, if the water content of the mobile phase is high, or becomes high due to the gradient used, it is difficult to achieve/maintain a stable spray, and consequently, the sensitivity of the analysis deteriorates. However, despite its disadvantages as a solvent, it is often necessary or desirable to use water in the mobile phase to elute polar solutes.

SUMMARY

Exemplary embodiments of the present technology are directed to microfluidic liquid chromatography-electrospray ionization (LC-ESI) devices for use with a mass spectrometer (MS) and methods using the devices for enhancing ionization efficiency. In some embodiments, an enhancement of ionization efficiency results in an increase in the sensitivity of detection of analytes present in a sample. In general, efficient ionization throughout the chromatography process results in increased detection sensitivity because it leads to a stable spray of charged droplets containing analyte ions. In prior art electrospray ionization procedures, obtaining stable spray in LC-ESI-MS was challenging as the water content in the mobile phase increased (e.g., in LC-ESI-MS utilizing mobile phase gradients designed for eluting polar solutes). In the devices and methods disclosed herein, a post-column modifier reagent is added to the eluate of the liquid chromatography column in a manner effective to achieve optimal mixing of the two for obtaining greater and/or maintaining conditions of stable spray, thereby enhancing sensitivity of detection in LC-ESI-MS. In one embodiment, the post-column modifier comprises an organic solvent. In one embodiment, the post-column modifier is an organic solvent selected from the group consisting of: hexane, carbon tetrachloride, 2-chloro propane, chloroform, dichloromethane, tetrahydrofuran, diethyl ether, ethyl acetate, dioxane, acetronitrile, propanol, isopropanol, methanol and acetic acid. In particular, the post-column modifier is added after chromatographic separation in a microfluidic device. The post-column modifier may be combined with the eluate at an edge of the electro spray emitter of the microfluidic device. As a consequence, efficient intermixing of the post-column modifier and the eluate is achieved. In another embodiment, the post-column modifier may be combined with the eluate in any manner appropriate to ensure sufficient mixing.

In accordance with an aspect of the present disclosure, a device for enhanced detection of an analyte in a sample is provided. The device includes a first inlet port fluidly connected to an analytical fluid stream and a second inlet port in fluid communication with a pump for delivering a post-column modifier reagent. Further, an ESI emitter is included, the emitter having a proximal end and a distal end and defining an emitter flow path between the two ends. The proximal end includes an interface portion adapted to receive and mix the analytical fluid stream and the post-column modifier reagent to form a mixed flow stream. The distal end includes a distal tip portion adapted to eject the mixed flow stream. An analytical microfluidic channel included in the device is fluidly connected to the first inlet port and extends to the proximal end of the emitter. Further, a fluid delivery microfluidic channel is included which is connected to the second inlet port and also extends to the proximal end of the emitter. The interface portion includes a longitudinally extending flow path adapted to receive the analytical flow stream from the analytical microfluidic channel. The interface portion also includes a laterally extending flow path disposed about the longitudinally extending flow path and adapted to receive the post-column modifier reagent. A flow diversion device is positioned between the two flow paths. The flow diversion device is shaped to drive mixing of the analytical fluid stream and the post-column modifier reagent. This optionally may occur at an outer wall of the laterally extending flow path. The longitudinal and laterally extending flow paths are fluidly connected by a connecting flow path.

Embodiments of the above apparatus can include one or more of the following features. In one embodiment, the analytical microfluidic channel has an inner diameter in the range of about 100 μm to about 200 μm. In one embodiment, the analytical microfluidic channel has an inner diameter of about 150 μm. In one embodiment, the length of the analytical microfluidic channel is between about 20 mm and 300 mm. In another embodiment, the analytical microfluidic channel length is between about 50 mm and about 100 mm. In one embodiment the analytical microfluidic channel is packed with silica particles. In one embodiment, the analytical microfluidic channel is packed with 1.7 μm silica particles. In either of the previous two embodiments, the silica particles may be functionalized. For example, in this embodiment, the silica particles may be functionalized with one of: C4, C8, C18, phenyl-hexyl, embedded-polar, amide, diol, and cyano. In one embodiment the flow diversion device has a curvilinear shape. For example, the flow diversion device is shaped like a C. In another embodiment, the flow diversion device has a cone shape. In another embodiment, the flow diversion device has any shape which can allow for ample mixing of the eluate and post-column modifying reagent. In one embodiment the analytical microfluidic channel and the fluid delivery microfluidic channel are contained within a ceramic housing. In one embodiment the distal tip portion is in fluid communication with a mass spectrometer. In one embodiment, the device further includes a gradient stream inlet fluidly connected to the analytical microfluidic channel. In one embodiment, the pump is adapted to vary flow rate of the post-column modifier reagent according to a feedback received by the pump. In one embodiment, the feedback is based on the magnitude of capillary current produced by the electrospray produced at the distal tip portion.

Further, in accordance with an aspect of the present disclosure, a method is provided for enhanced detection of an analyte in a sample in liquid chromatography electrospray ionization (LC-ESI) analysis involving the use of a gradient mobile phase. The method includes the steps of: providing a LC-ESI device including a first inlet port fluidly connected to an analytical fluid stream; a second inlet port in fluid communication with a pump for delivering a post-column modifier reagent; an ESI emitter, the emitter having a proximal end and a distal end and defining an emitter flow path therebetween, the proximal end including an interface portion adapted to receive and mix an eluate from the analytical microfluidic channel and the post-column modifier reagent to form a mixed flow stream, the distal end including a distal tip portion adapted to eject the mixed flow stream; an analytical microfluidic channel fluidly connected to the first inlet port and extending to the proximal end of the emitter; and a fluid delivery microfluidic channel fluidly connected to the second inlet port and extending to the proximal end of the emitter; applying the sample to the analytical microfluidic channel; eluting the analyte under the gradient mobile phase condition; flowing the post-column modifier reagent through the fluid delivery channel at a varying rate so as to maintain an organic solvent content of the mixed flow stream at a pre-determined value throughout the gradient; and, analyzing ions of the analyte present in the mixed flow stream using a mass spectrometer.

Embodiments of the above method can include one or more of the following features. In one embodiment of the method, the organic solvent component of the mixed flow stream is at least: about 25%; about 24%; about 23%; about 22%; about 21%; or about 20%. In another embodiment, the organic solvent component of the mixed flow stream is at least: about 30%, about 35% or about 40%. In one embodiment, the post-column modifier reagent includes an organic solvent which is the same as that in the analytical flow stream. Alternatively, the post-column modifier reagent includes an organic solvent that is different from that in the analytical flow stream. In one embodiment, the mobile phase comprises dimethyl sulfoxide and/or ammonium fluoride. In one embodiment, the mobile phase comprises dimethyl sulfoxide, ammonium fluoride, ammonium hydroxide and/or ammonium bicarbonate.

According to another aspect of the present disclosure another method is provided for enhanced detection of an analyte in a sample in liquid chromatography electrospray ionization (LC-ESI) analysis. The method includes: providing a LC-ESI device including a first inlet port fluidly connected to an analytical fluid stream; a second inlet port in fluid communication with a pump for delivering a post-column modifier reagent; an ESI emitter, the emitter having a proximal end and a distal end and defining an emitter flow path therebetween, the proximal end including an interface portion adapted to receive and mix an eluate from the analytical microfluidic column and the post-column modifier reagent to form a mixed flow stream, the distal end including a distal tip portion adapted to eject the mixed flow stream; an analytical microfluidic channel fluidly connected to the first inlet port and extending to the proximal end of the emitter; and a fluid delivery microfluidic channel fluidly connected to the second inlet port and extending to the proximal end of the emitter; applying the sample to the analytical microfluidic channel; eluting the analyte; flowing the post-column modifier reagent through the fluid delivery channel at a selected flow rate; measuring organic solvent content of the mixed flow stream at the distal tip portion; comparing the measured organic solvent content to a pre-determined value; varying the selected flow rate to maintain an organic solvent content of the mixed flow stream at a pre-determined value throughout the chromatography; and, analyzing ions of the analyte present in the mixed flow stream using a mass spectrometer.

Embodiments of the methods described in the preceding paragraphs can include one or more of the following features. In one embodiment, the organic solvent content is measured based on the magnitude of capillary current produced by an electrospray formed at the distal tip portion. In one embodiment, the analyte is eluted using a mobile phase of fixed composition. Alternatively, the analyte is eluted using a gradient mobile phase. In one embodiment, the electrospray ionization is performed in a negative ionization mode. Alternatively, the electrospray ionization is performed in a positive ionization mode. In one embodiment, the modifier reagent includes an organic solvent which is the same as that in the analytical flow stream. Alternatively, the modifier reagent includes an organic solvent that is different from that in the analytical flow stream. In one embodiment, the modifier reagent includes an organic solvent selected from the group comprising: methanol, acetonitrile, propanol, and isopropanol. In one embodiment, the organic solvent component of the mixed flow stream is at least: about 25%; about 24%; about 23%; about 22%; about 21%; or about 20%. In one embodiment, the mobile phase comprises dimethyl sulfoxide and/or ammonium fluoride. In one embodiment, the mobile phase comprises dimethyl sulfoxide, ammonium fluoride, ammonium hydroxide and/or ammonium bicarbonate.

The exemplary device and methods of the present disclosure provide several advantages. For example, analytes that elute under mobile phase conditions having low organic solvent content, and were either undetectable by LC-ESI-MS or detectable unreliably due to poor sensitivity, may now be reliably detected with the device disclosed herein for adding a post-column modifier reagent to the analytical flow stream exiting a chromatography stationary phase (eluate). Similarly, analytes eluting in mobile phases having low organic solvent content, which were being detected only poorly, i.e. the detection was not quantitative, may now be quantitatively detected with the addition of a post-column modifier reagent.

BRIEF DESCRIPTION OF THE DRAWINGS

The foregoing and other features and advantages provided by the present disclosure will be more fully understood from the following description of exemplary embodiments when read together with the accompanying drawings, in which:

FIG. 1 is a Negative Electrospray Ionization (ESI-) Time of Flight (TOF) Mass Spectrometry (MS) profile of an enzymatic digest of a protein separated using liquid chromatography (LC), and analyzed using ESI-MS without using a post-column modifier reagent.

FIG. 2 is a ESI-TOF MS profile of total lipid extract from a liver, which was obtained without using a post-column modifier reagent.

FIG. 6A shows details of the junction between the microfluidic channels and the interior of the emitter. FIG. 6B shows the junction with a seal to confine the eluate and the post-column modifier reagent within the emitter. FIG. 6C shows a view of the flow paths of the analytical fluid stream and the post-column modifier reagent.

FIG. 8 is a flow chart of another method for enhanced detection of an analyte in a sample using an LC-ESI device disclosed herein in which the pump used for delivering the post-column modifier reagent delivers the reagent according to a feedback received by the pump, the feedback being generated based upon the magnitude of capillary current produced by the electrospray.

FIG. 9A shows a view of the interior of one end of the emitter of another exemplary microfluidic LC-ESI device described herein, at which the analytical and the post column infusion channels connect with the emitter. FIG. 9B shows a view of the junction between microfluidic channels and the interior of the emitter at the same end (FIG. 9A) of the emitter.

FIG. 11 is a graph of the flow rate of the post-column modifier reagent plotted against percent organic solvent (acetonitrile) content of the mobile phase gradient for three different flow rates of the mobile phase. A curve corresponding to a specific mobile phase flow rate depicts the optimal flow rate of the modifier reagent for that mobile phase flow rate during the entirety of the chromatographic process.

DETAILED DESCRIPTION

Figure 3A:
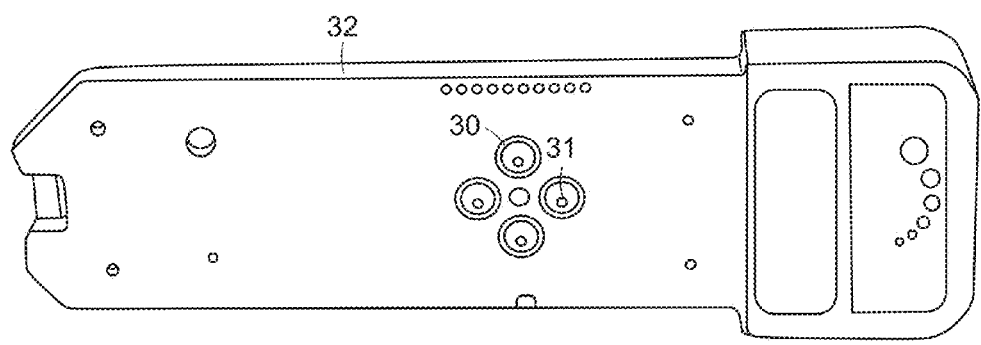
FIG. 3A shows a view of one side of an exemplary microfluidic LC-ESI device described herein.

The sensitivity of detection of an analyte using LC-ESI-MS is strongly dependent on the ionization efficiency of the analyte. Ionization efficiency depends upon efficient generation of a spray of charged droplets of the mobile phase at the tip of the capillary tube of the ESI interface, and upon efficient evaporation of the mobile phase as the droplets migrate toward the mass spectrometer. The charged droplets contain target ions, i.e., ions of the analyte.

Maintenance of the sensitivity of detection during the entirety of a chromatographic run requires that a spray produced be stable throughout the run. In a chromatographic separation involving a gradient of an organic solvent and another solvent having relatively high surface tension and conductivity (e.g. water), the content of the latter in the mobile phase may increase—eventually reaching a level beyond which generation of the charged droplets, as well as evaporation of the mobile phase from the droplets, becomes inefficient. Alternatively, the proportion of the solvent with high surface tension and conductivity may be high in the beginning of the gradient as in the case of a reverse phase chromatographic separation. Both cases may result in a failure to maintain a stable spray, and consequently, a failure to maintain high sensitivity of detection.

FIG. 1 provides an example of an LC-ESI-MS based analysis performed without the addition of a post-column modifier reagent. The analysis depicted is that of an enzymatic digest of a protein separated using liquid chromatography (LC), and analyzed using ESI and Time of Flight (TOF) MS. The ionization was performed in the negative ionization mode. A mixture of two mobile phases A, and B was used in a gradient consisting of increasing amounts of B. The composition of A was Water+0.1% Formic Acid (FA), and that of B was Acetonitrile (ACN)+0.1% FA. A region is indicated in the lower m/z part of the spectrum where expected peaks are missing. This part of the spectrum corresponds to elution in the presence mostly of A, i.e. water, with little acetonitrile. Another arrow points to an unstable ion signal. The region of missing peaks and the unstable peak strongly indicate that spray was not stable, both in the beginning, and well into the analysis. In particular, the result shown in FIG. 1 indicates that the spray was poor when elution was taking place in mobile phase containing water as the major solvent. At this stage the organic solvent content was less than 20%. As a result, the chromatographic analysis is flawed.

In contrast to the above example, FIG. 2 exemplifies a LC-ESI-MS based separation in which the sensitivity of detection was high throughout the analysis, indicating that a stable spray was maintained during the entire time period of the analysis. In this case also no post-column modifier reagent was added to the column eluate. Shown in FIG. 2 is a Negative Electrospray Ionization Time of Flight Mass Spectrum (TOF MS ES-) of total lipid extracts from liver. A mixture of two mobile phases, A and B was used for this separation also. The mobile phase A was composed of ACN:Water (60:40) with 10 mM ammonium formate and 0.1% FA. The mobile phase B was composed of isopropyl alcohol (IPA):ACN (90:10) with 10 mM ammonium formate and 0.1% FA. Among the lipids detected in the spectrum are PC (phosphatidylcholine), SM (sphingomyelin), PE (phosphatidylethanolamine), PG, PI (phosphatidylinositol), FFA (free fatty acid), and LP (lysophospholipids). Because of the high organic solvent content in both A and B, at all stages of the chromatography, the elution took place in the presence of at least 60% organic solvent.

Comparison of the results of FIGS. 1 and 2 shows that in LC-ESI-MS based detection of analytes in which the organic solvent component in the mobile phase is low (as in the missing peak region of the chromatogram in FIG. 1), detection of certain analytes by ESI-MS may not be sensitive. Therefore, there is a need for improving detection sensitivity in such situations. The problem of poor detection sensitivity in LC-ESI-MS may be solved by the addition of a post-column modifier reagent to the eluate to maintain the organic solvent content at a level high enough for generating a stable spray. However, a stable spray does not result by mere addition of a modifier reagent to the eluate. The modifier reagent and the eluate has to be mixed adequately for the addition of the modifier reagent to be effective in achieving/maintaining a stable spray throughout the chromatographic run.

As a solution to the problem of the failure to maintain a stable spray in LC-ESI-MS, described herein is a LC-ESI microfluidic device and methods using the device, in which the post-column modifier reagent is added to the eluate in a manner that permits optimal mixing of the two fluids. A flow stream of the mixture thus produced is ejected from the ESI capillary to generate an electrospray containing analyte ions for detection by a mass spectrometer. The enhanced sensitivity of detection obtained by using the device and methods herein is achieved in a few different ways. Firstly, an emitter interface is used that receives the eluate and the post-column modifier reagent from two separate flow paths and drives extensive intermixing of fluids in the two flow paths to generate a mixed flow stream for ejecting through the ESI capillary. Secondly, a method, using the emitter interface, is implemented in which the modifier pump is programmed to deliver the post-column modifier reagent at varying flow rates such that the flow rate at any instant during the chromatography is sufficient to maintain the organic solvent content in the mixture (i.e., the mixed flow stream) at a pre-determined level. The organic solvent content of the mixture would otherwise vary according to the mobile phase gradient used in the separation. The pre-determined level of organic solvent content is that amount of organic solvent, which when present in the mixture, is sufficient for mass spectrometric detection of an analyte present in the mixture (e.g., no unstable ion signal or missing peaks). Additionally, another method, also using the emitter interface is disclosed herein, in which the modifier pump is able to increase or decrease the flow rate of the modifier reagent in response to feedback received by the pump. The feedback is generated based on the magnitude of capillary current produced by the electrospray formed at the capillary tip. A low capillary current indicates insufficient organic solvent content in the mixture, to which the pump responds by increasing the flow rate at which the post-column modifier reagent is added to the eluate. Enhanced stability is achieved by implementing one or more of the above methods and devices.

In general, the LC-ESI microfluidic device, in accordance with the present technologies, includes a microfluidic channel packed with a stationary phase for liquid chromatography, another microfluidic channel for delivering the post-column modifier reagent to the liquid chromatography eluate, and an ESI emitter for the production of an electrospray containing an analyte. FIG. 3A is a view of one side of the LC-ESI microfluidic device showing four ports (e.g.

Figure 3B:
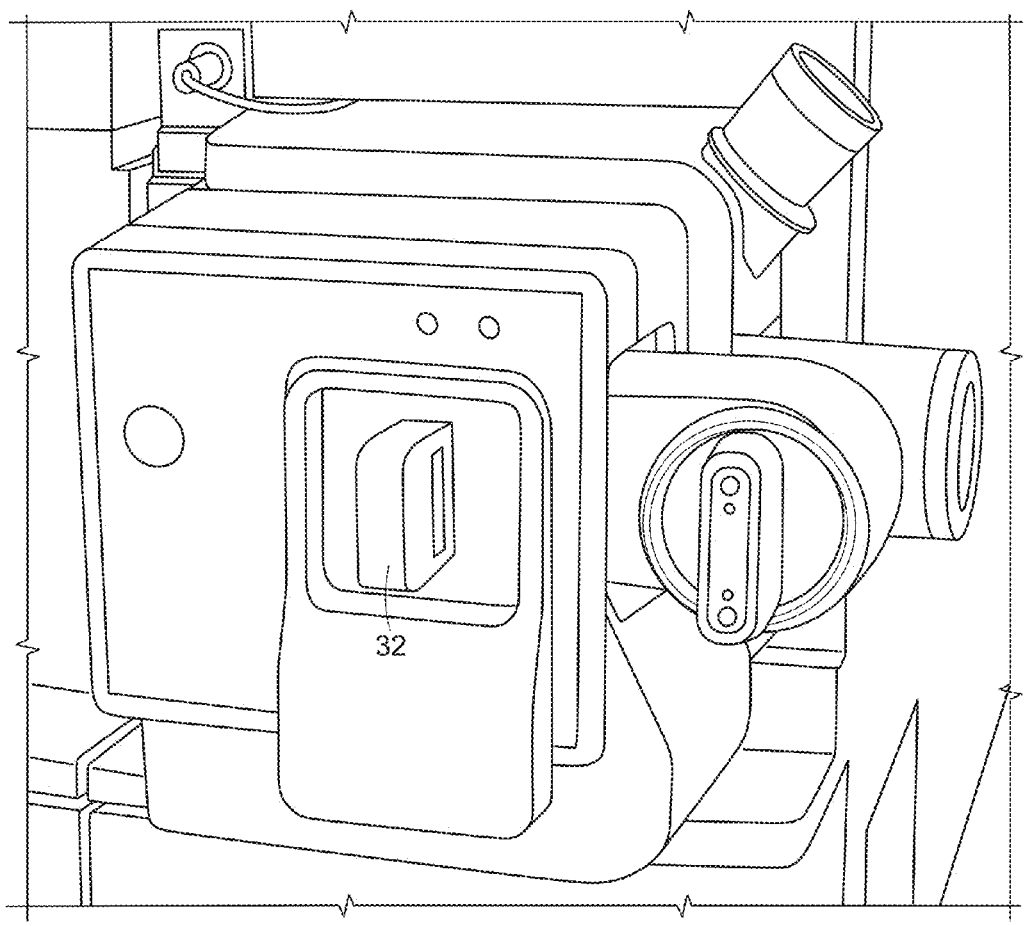
FIG. 3B shows the LC-ESI device integrated into an apparatus for generating analyte ions from the electrospray for analysis by a mass spectrometer.

30 and 31) that receive different fluids including the mobile phase used in the chromatography and the post-column modifier reagent. The post-column modifier reagent generally consists of a solvent that increases the organic content of the fluid passing through the ESI device. FIG. 3B shows the integration of the LC-ESI device (32) into an apparatus for generating analyte ions from the electrospray for analysis by a mass spectrometer. In some embodiments, the apparatus also includes a modifier pump to add the post-column modifier reagent in a controllable manner.

Figure 4:
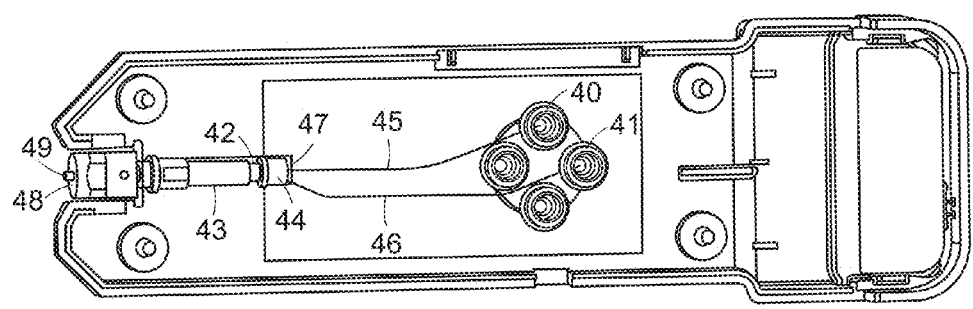
FIG. 4 shows additional internal features of the microfluidic LC-ESI device shown in FIG. 3A.

Additional features of the LC-ESI microfluidic device (32) are shown in FIG. 4. In FIG. 4, an outer portion (i.e. housing) has been removed so that the internal components of the device can be viewed. The Figure shows receptacles (40) and (41) which receive the mobile phase and the post-column modifier reagent, respectively. The receptacles (40) and (41) are fluidly connected to port (30) and port (31) shown in FIG. 3A. That is, port (30) is connected to receptacle (40), and port (31) is connected to receptacle (41). The device (32) further includes an emitter (42) enclosed in a protective housing (43) with a proximal end (47) and a distal end (48). The distance between the proximal end (47) and the distal end (48) defines an emitter flow path. The emitter (42) includes an interface portion (44) adapted to receive and mix an analytical flow stream, that has passed through a chromatographic stationary phase, with the post-column modifier reagent, to form a mixed flow stream. The distal end (48) of the device (32) includes a distal tip portion (49) or a capillary adapted to eject the mixed flow stream. The device (32) includes an analytical microfluidic channel (45), and a fluid delivery microfluidic channel (46). The analytical microfluidic channel (45) is packed with a stationary phase suitable for the separation of the analytes present in a sample. The analytical microfluidic channel (45) is fluidly connected to the receptacle (40) for receiving the necessary mobile phase, and extends to the proximal end (47) of the emitter. The fluid delivery microfluidic channel (46) is shown fluidly connected to the receptacle (41). In some embodiments, the receptacle (41) can be adapted to be in fluid communication with a pump for delivering the post-column modifier reagent in a controlled manner. The fluids eluting from the analytical channel (45) and the fluid delivery channel (46) are mixed together prior to leaving the distal end (48) of the emitter (42). That is, the sample, after chromatographic separation, and the post-column modifier reagent are mixed together prior to ejection from the emitter. In the embodiment shown in FIG. 4, the fluid eluting from the analytical channel (45) and the fluid from the fluid delivery channel (46) mix at the interface portion (44) at the proximal end (47) of the emitter (42).

Figure 5:
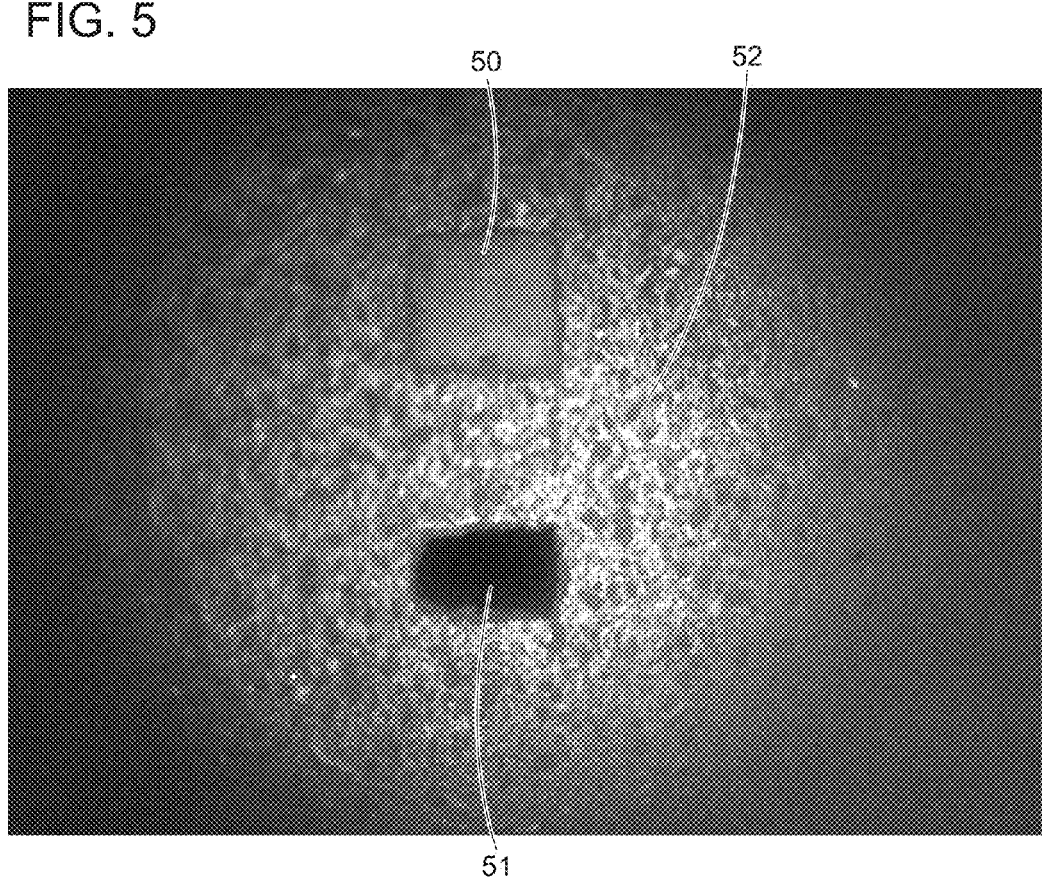
FIG. 5 shows a view of the surface of one end of the emitter at which two microfluidic channels, one for delivering an eluate (analytical fluid stream) and the other for delivering a post-column modifier reagent meet the emitter.

The outer surface of the interface portion (44) is shown in FIG. 5. Shown on the surface are regions (50) and (51) at which the fluid delivery microfluidic channel (46), for delivering the post-column modifier reagent) and the analytical microfluidic channel (45) meet the interface portion (44). In this embodiment the LC-ESI microfluidic device (32) is made of a ceramic material, and therefore, surface (52) is a ceramic surface. The device could be made from other material, for example, a metal or a metal ceramic composite.

Figure 6A:
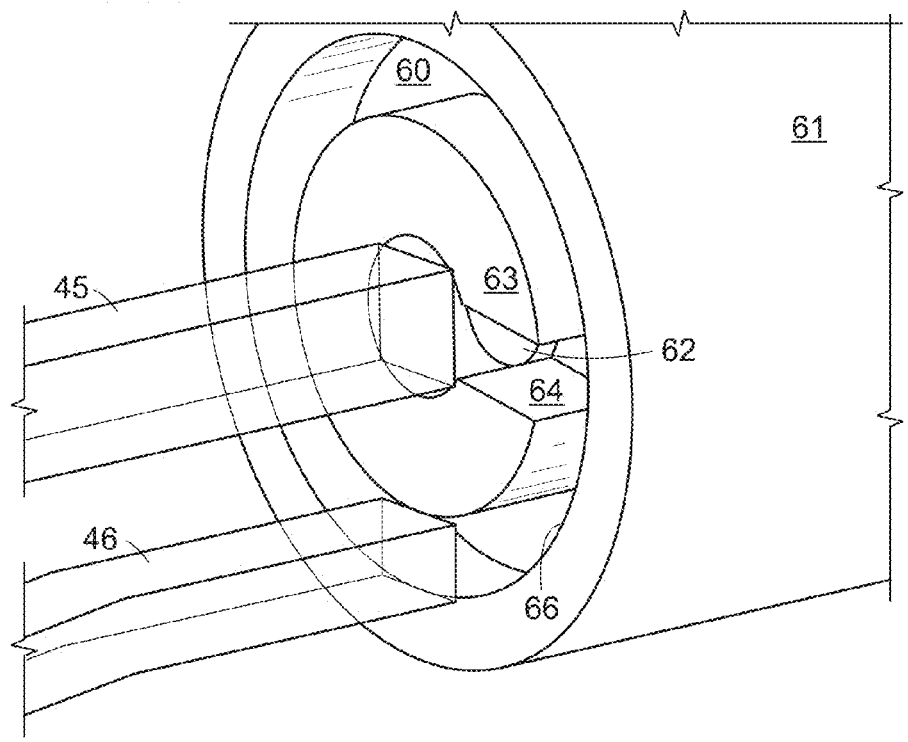
FIGS. 6A-6C show different views of the junction between the analytical and the post-column infusion channels, and the emitter.
Figure 6B:
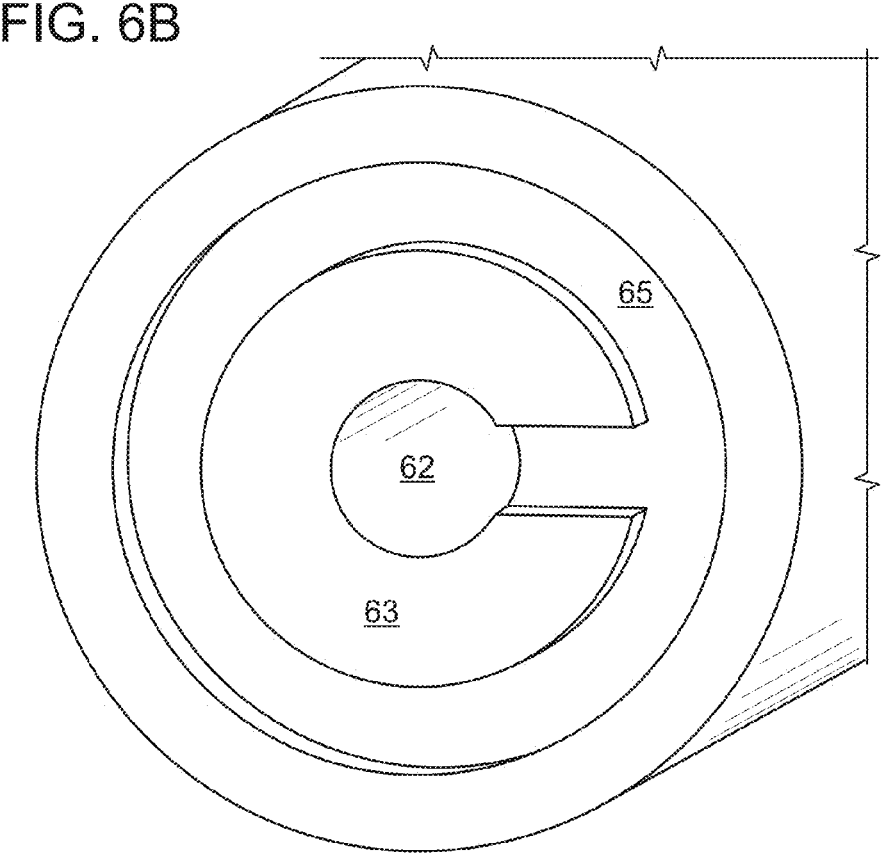
Figure 6C:
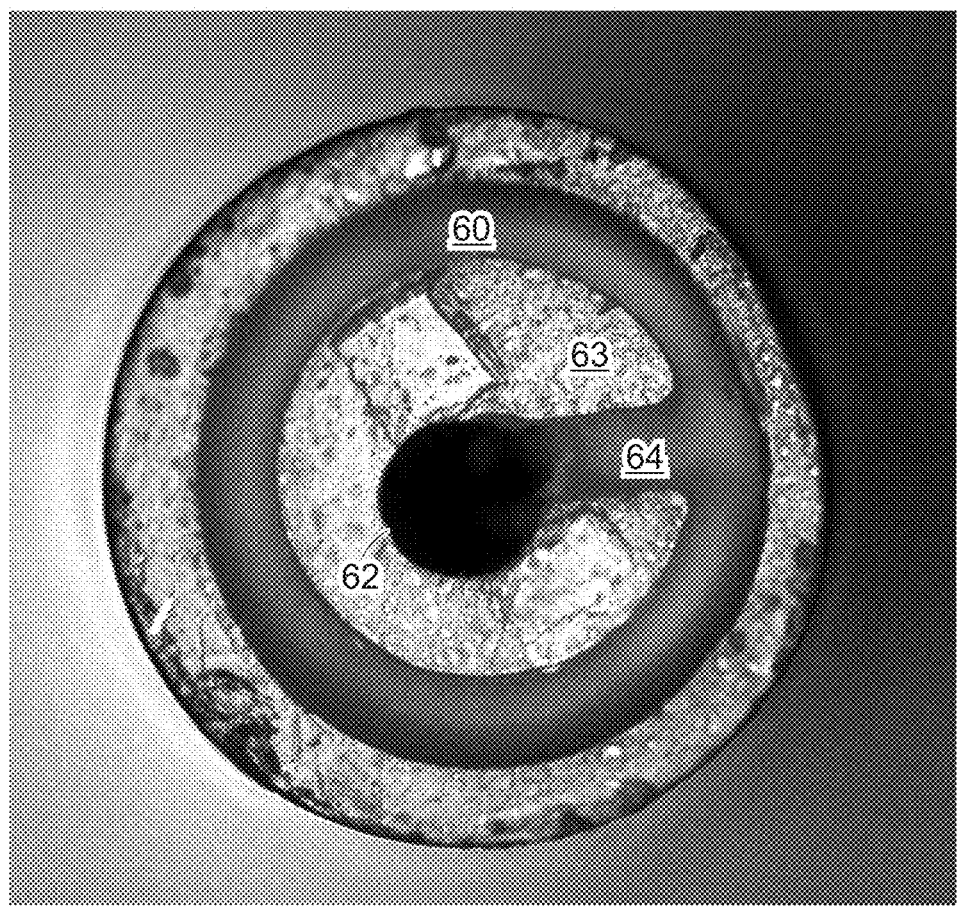

The emitter interface portion (44) is shown in greater detail in FIGS. 6A-6C. FIG. 6A shows details of the junction between the microfluidic channels (45 and 46) and an interior of the emitter. The interface portion (44) includes a longitudinally extending flow path (62) adapted to receive the analytical flow stream from the analytical microfluidic channel (45). As seen in FIG. 6C, the interface portion further includes a laterally extending flow path (60) disposed about the longitudinally extending flow path (62) and adapted to receive the post-column modifier reagent (i.e., flow from the fluid delivery channel (46)). A flow diversion device (63) is positioned between the longitudinally and the laterally extending flow paths. The flow diversion device (63) has a shape designed to drive mixing of the analytical fluid stream and the post-column modifier reagent at an outer wall (66) of the laterally extending flow path (60). The longitudinally (62) and the laterally (60) extending flow paths are fluidly connected by a connecting flow path (64). The laterally extending flow path (60) and the connecting flow path (64) combined form a mixing chamber for mixing the analytical fluid stream containing one or more analytes and the post-column modifier reagent. The outer surface of the emitter shown in FIG. 6A is marked (61). The view of the interface shown in FIG. 6B further shows a seal (65) used to confine fluids within the emitter (42). By forcing the two flow streams (i.e., fluids from the analytical microfluidic channel (45) and the fluid delivery channel (46) to mix at an outer edge of the interface portion, a homogenous mixed fluid is formed. While not wishing to be bound by any particular theory or mechanism, it is believed that by driving mixing at an outer edge, the fluids can be mixed over an extended area, resulting in better mixing in a confined space. For example, in one embodiment, the mixing begins in the connecting flow path (64) and continues at the laterally extending flow path (60) owing to the greater flow rate of the analytical fluid stream compared to a lesser flow rate of the modifier reagent flowing through the fluid delivery channel (46).

Figure 7:
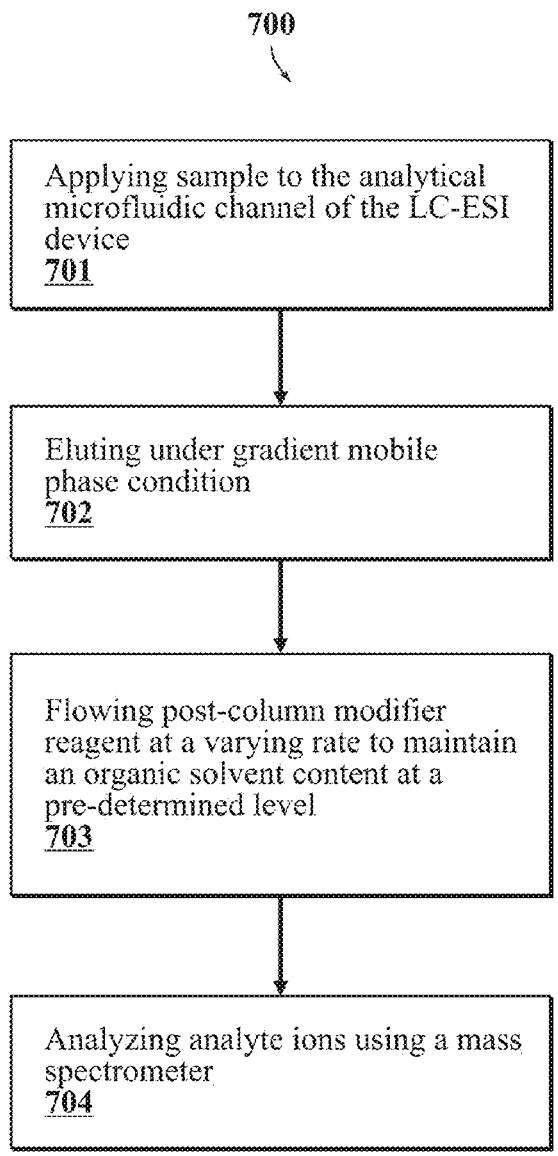
FIG. 7 is a flow chart of a method for enhanced detection of an analyte in a sample using a LC-ESI device disclosed herein in which the pump used for delivering the post-column modifier reagent is programmed to maintain the organic solvent content of the eluate exiting the analytical microfluidic channel at a pre-determined level.

Further described herein are methods for enhanced detection of an analyte in a sample using the LC-ESI device described above. In one embodiment, a method is directed to enhancing detection in an LC-ESI-MS analysis in which a gradient mobile phase is used in the chromatographic separation. In particular, this method provides for enhanced stability over conventional methods, as it addresses changes in organic solvent content in the mixed fluid stream that would result from the changing organic solvent content in the analytical fluid stream caused by the gradient. That is, the method includes varying (i.e., increasing or decreasing) the flow rate of the post-column modifier fluid to "make-up" for a predetermined or known decrease in organic solvent content as a result of a planned solvent gradient. The various steps included in the method (700) are shown in FIG. 7. These steps are: applying the sample to the analytical microfluidic channel of the device (step 701); eluting the analyte under a gradient mobile phase condition; (step 702); flowing the post-column modifier reagent through the fluid delivery channel at a varying rate so as to maintain an organic solvent content of the mixed flow stream at a pre-determined value throughout the gradient (step 703); and, analyzing ions of the analyte present in the mixed flow stream using a mass spectrometer (step 704). The pre-determined level of organic solvent content is chosen to be an amount of organic solvent, that, when present in the mixture is sufficient for generating an analyte signal readily detected by a mass spectrometer.

For example, enhanced detection may be obtained by implementing the above method, thereby maintaining a desired level of organic solvent in the mixed flow stream flowing through the emitter. First, an organic solvent content value for the mixed fluid ejected from the emitter is selected. In one embodiment, this value, the pre-determined organic solvent content value, is about 25%. This value is entered into the controller of the modified pump. Next, the mobile phase gradient to be used in the separation is analyzed to determine the extent to which the organic solvent content of the gradient falls short of the pre-determined value. The modifier pump is then programmed to increase the rate at which the modifier reagent is introduced to make up for the shortfall of organic solvent in the eluent coming from the analytical microfluidic channel as the gradient progresses.

In another embodiment of the method for enhanced detection of an analyte using the LC-ESI device described above, a modifier pump controlling flow of the reagent is introduced and used to vary the flow rate of the post-column modifier reagent in accordance with feedback received by the pump. The feedback is generated based on the magnitude of capillary current produced by the electrospray formed at the capillary tip. Organic solvent content below a certain level in the mixture produces a low capillary current, to which the pump responds by increasing the flow rate at which the post-column modifier reagent is added to the eluate. Steps included in this embodiment of the method (800) are shown in FIG. 8. These steps are: applying the sample to the analytical microfluidic channel of the device (801); eluting the analyte (802); flowing the post-column modifier reagent through the fluid delivery channel at a selected flow rate (803); measuring organic solvent content of the mixed fluid stream at the distal tip portion (804); comparing the measured organic solvent content to a pre-determined value (805); varying the selected flow rate to maintain an organic solvent content of the mixed fluid stream at a pre-determined value throughout the gradient (806); and, analyzing ions of the analyte present in the mixed fluid stream using a mass spectrometer (807).

For example, the above method for providing enhanced stability could be implemented, as described in the following, by monitoring and updating (i.e., regulating) the content of organic solvent in the mixed fluid stream flowing through the emitter. First, a value of organic solvent content for the mixed solvent ejected from the emitter is selected. In one embodiment, this value, the pre-determined value, is about 30%. This value is entered into a control system, which provides feedback information to the modifier pump such that the flow rate of the post-column modifier reagent can be modified during an analysis to provide enhanced results. A sensor placed in communication with the capillary of the emitter measures the current emitted therefrom. The measured current is translated to a % organic solvent, for example, by means of an algorithm. The % organic solvent thus obtained is compared to the pre-determined organic content value, and if found to be lower, the modifier pump controller is updated to increase flow of the post-column reagent.

While the above embodiments have been described using the interface portion (44) within the LC-ESI device (32), the methods above may also be implemented using the LC-ESI device (32) and other interface portion designs/embodiments. For example, the interface portion (95) shown in FIG. 9B can be used in one or more of the above methods. This emitter interface (95) has a cone shaped space (91) for the mixing of the analytical fluid stream containing one or more analyte and the post-column modifier reagent. (See FIGS. 9A and 9B). The outer surface of the emitter is marked (90). Unlike the emitter interface (44) shown in FIGS. 6A and 6B, in this case there is no separation between the fluid paths or the spaces to which the analytical fluid stream and the post-column modifier reagent are added. FIG. 9B shows a view of the junction between the analytical and the fluid delivery microfluidic channels (93) and (94), and the cone shaped space (91) inside the emitter where the mixing between the analytical fluid stream and the post-column modifier reagent takes place. Both microfluidic channels deliver fluid at the edge of the cone shaped space (91). In one embodiment, the mixed fluid can then be transferred through the emitter port (92) to the mass spectrometer for analysis.

Figure 10:
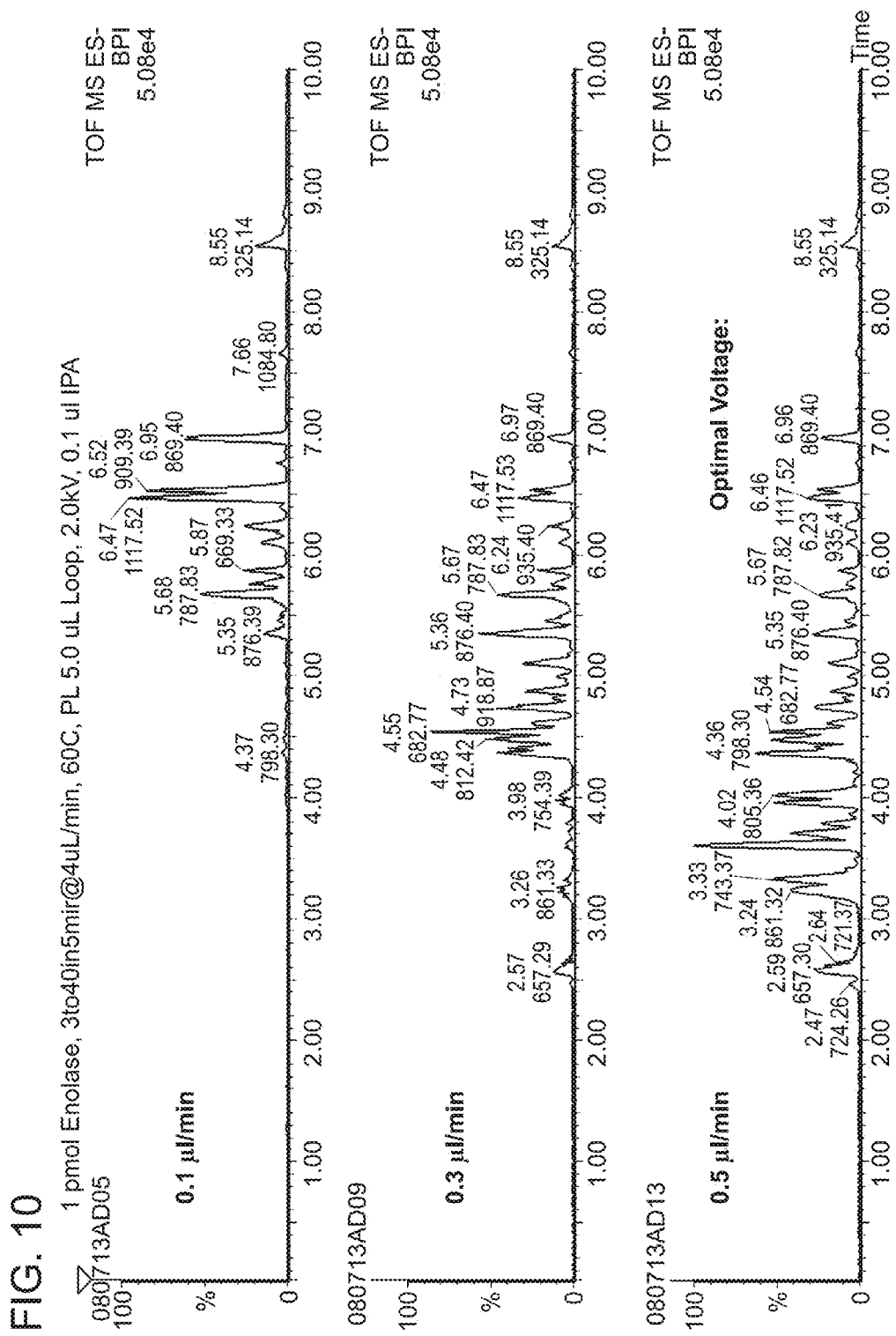
FIG. 10 shows three ESI-MS profiles for the separation of peptides obtained from tryptic digest of enolase. The profiles differ in that they show the results of the addition of different amounts of a modifier reagent to the column effluent.

Enhancement of the sensitivity of detection obtained by using the devices and methods described herein is exemplified by the separation and detection of peptides obtained from enolase digested with trypsin (FIG. 10). In each of the three separations shown in FIG. 10, Isopropyl alcohol (IPA) was added as the post-column modifier reagent. The three ESI-MS profiles differ in the amount of modifier reagent that was added to the eluate or the analytical fluid stream exiting the analytical microfluidic channel. In the range tested, the best result was obtained when the modifier reagent was added at the flow rate of 0.5 µL/min. The flow rate of the mobile phase was 4 µL/min. Several additional peaks were observed in the lower m/z part of the ESI mass spectrum corresponding to the two higher flow rates of the modifier reagent, indicating that adding the modifier reagent at the flow rate of 0.1 µL/min was not sufficient to bring the organic solvent content in the mixed flow stream to a level necessary for generating an electrospray that could be desolvated efficiently to generate analyte ions.

Optimal results for enhancement of sensitivity of detection, using the method described herein, depends upon the flow rates of both the eluate and the post column modifier reagent. In FIG. 11 a plot of the flow rate of the post-column modifier reagent against percent organic solvent (acetonitrile) content of the mobile phase gradient is shown for three different flow rates of the mobile phase. Each curve corresponds to a specific mobile phase flow rate. Curves (1110), (1120), and (1130) correspond to mobile phase flow rates of 4 µL/min, 3 µL/min, and 2 µL/min, respectively. It can be seen from the graph that a higher post-column modifier flow rate is needed when the organic solvent content of the gradient is low. Further, a higher mobile phase flow rate generally requires a higher flow rate for the addition of the post-column modifier reagent during stages of chromatography when the organic solvent content in the mobile phase gradient is low.

While exemplary embodiments have been described herein, it is expressly noted that these embodiments should not be construed as limiting, but rather that additions and modifications to what is expressly described herein also are included within the scope of the invention. Moreover, it is to be understood that the features of the various embodiments, such as using negative ionization electrospray, and adding the modifier reagent as a gradient, are not mutually exclusive and can exist in various combinations and permutations, even if such combinations or permutations are not made express herein, without departing from the spirit and scope of the technology.

What is claimed is:

1. A microfluidic liquid chromatography-electrospray ionization (LC-ESI) device for enhanced detection of an analyte in a sample, the device comprising:
   a first inlet port fluidly connected to an analytical fluid stream;
   a second inlet port in fluid communication with a pump for delivering a post-column modifier reagent;
   an ESI emitter, the emitter having a proximal end and a distal end and defining an emitter flow path therebetween, the proximal end including an interface portion adapted to receive and mix the eluate from an analytical microfluidic channel and the post-column modifier reagent to form a mixed flow stream, the distal end including a distal tip portion adapted to eject the mixed flow stream;

an analytical microfluidic channel fluidly connected to the first inlet port and extending to the proximal end of the emitter; and a fluid delivery microfluidic channel fluidly connected to the second inlet port and extending to the proximal end of the emitter;

wherein the interface portion comprises a longitudinally extending flow path adapted to receive the analytical flow stream from the analytical microfluidic channel; a laterally extending flow path disposed about the longitudinally extending flow path and adapted to receive the post-column modifier reagent, and a flow diversion device positioned therebetween, the flow diversion device being shaped to drive mixing of the eluate from the analytical microfluidic channel and the post-column modifier reagent; and a connecting flow path which fluidly connects the longitudinal and laterally extending flow paths.

2. The device according to claim 1, wherein the analytical microfluidic channel has an inner diameter of about 150 µm, and a length between about 50 mm and about 100 mm.

3. The device according to claim 1, wherein the analytical microfluidic channel is packed with 1.7 µm silica particles.

4. The device according to claim 3, wherein the silica particles are functionalized.

5. The device of claim 4, wherein the functional group is selected from the group consisting of: C4, C8, C18, phenyl-hexyl, embedded-polar, amide, diol, and cyano.

6. The device according to claim 1, wherein the flow diversion device has a curvilinear shape.

7. The device according to claim 6, wherein flow diversion device is shaped like a C.

8. The device according to claim 1, wherein the analytical microfluidic channel and the fluid delivery microfluidic channel are contained within a ceramic housing.

9. The device according to claim 1, wherein the distal tip portion is in fluid communication with a mass spectrometer.

10. The device according to claim 1, further comprising a gradient stream inlet fluidly connected to the analytical microfluidic channel.

11. The device according to claim 1, wherein the mixing of the eluate from the microfluidic channel and the post-column modifying reagent occurs at an outer wall of the laterally extending flow path.

12. The device according to claim 1, wherein the post-column modifying reagent is an organic solvent.

13. The device according to claim 1, wherein the pump is adapted to vary flow rate of the post-column modifier reagent according to a feedback received by the pump, wherein the feedback is based on a magnitude of capillary current produced by electrospray produced at the distal tip portion.

14. A method for enhanced detection of an analyte in a sample in a liquid chromatography electrospray ionization (LC-ESI) analysis using a gradient mobile phase, the method comprising:

providing a LC-ESI device including a first inlet port fluidly connected to an analytical fluid stream; a second inlet port in fluid communication with a pump for delivering a post-column modifier reagent; an ESI emitter, the emitter having a proximal end and a distal end and defining an emitter flow path therebetween, the proximal end including an interface portion adapted to receive and mix an eluate from the analytical microfluidic channel and the post-column modifier reagent to form a mixed flow stream, the distal end including a distal tip portion adapted to eject the mixed flow stream; an analytical microfluidic channel fluidly connected to the first inlet port and extending to the proximal end of the emitter; and a fluid delivery microfluidic channel fluidly connected to the second inlet port and extending to the proximal end of the emitter;

applying the sample to the analytical microfluidic channel;

eluting the analyte under the gradient mobile phase condition;

flowing the post-column modifier reagent through the fluid delivery channel at a varying rate so as to maintain an organic solvent content of the mixed flow stream at a pre-determined value throughout the gradient; and, analyzing ions of the analyte present in the mixed flow stream using a mass spectrometer.

15. The method of claim 14, wherein the organic solvent component of the mixed flow stream is at least about 20%.

16. A method for enhanced detection of an analyte in a sample in a liquid chromatography electrospray ionization (LC-ESI) analysis, the method comprising:

providing a LC-ESI device including a first inlet port fluidly connected to an analytical fluid stream; a second inlet port in fluid communication with a pump for delivering a post-column modifier reagent; an ESI emitter, the emitter having a proximal end and a distal end and defining an emitter flow path therebetween, the proximal end including an interface portion adapted to receive and mix an eluent from the analytical microfluidic channel and the post-column modifier reagent to form a mixed flow stream, the distal end including a distal tip portion adapted to eject the mixed flow stream; an analytical microfluidic channel fluidly connected to the first inlet port and extending to the proximal end of the emitter; and a fluid delivery microfluidic channel fluidly connected to the second inlet port and extending to the proximal end of the emitter;

applying the sample to the analytical microfluidic channel;

eluting the analyte;

flowing the post-column modifier reagent through the fluid delivery channel at a selected flow rate;

measuring organic solvent content of the mixed flow stream at the distal tip portion;

comparing the measured organic solvent content to a pre-determined value;

varying the selected flow rate to maintain an organic solvent content of the mixed flow stream at a pre-determined value throughout the chromatography; and, analyzing ions of the analyte present in the mixed flow stream using a mass spectrometer.

17. The method of claim 16, wherein the organic solvent content is measured based on the magnitude of capillary current produced by an electrospray formed at the distal tip portion.

18. The method of claim 16, wherein the analyte is eluted using a mobile phase of fixed composition.

19. The method of claim 16, wherein the analyte is eluted using a gradient mobile phase.

20. The method of claim 16, wherein the post-column modifier reagent comprises an organic solvent which is the same as that in the analytical flow stream.

21. The method of claim 16, wherein the post-column modifier reagent comprises an organic solvent different from that in the analytical flow stream.

\* \* \* \* \*